United States Patent
Festö

(10) Patent No.: US 7,090,863 B2
(45) Date of Patent: Aug. 15, 2006

(54) HYPOCHOLESTEROLEMIC COMPOSITION AND METHODS OF USE

(75) Inventor: Norberto Festö, Lugano (CH)

(73) Assignee: Inpharma S.A., Lugano (CH)

( * ) Notice: Subject to any disclaimer, the term of this patent is extended or adjusted under 35 U.S.C. 154(b) by 515 days.

(21) Appl. No.: 10/306,612

(22) Filed: Nov. 26, 2002

(65) Prior Publication Data

US 2003/0129217 A1 Jul. 10, 2003

Related U.S. Application Data

(60) Provisional application No. 60/338,402, filed on Nov. 30, 2001.

(51) Int. Cl.
*A61K 47/00* (2006.01)

(52) U.S. Cl. ...................................... 424/439

(58) Field of Classification Search ................ 424/426, 424/439
See application file for complete search history.

(56) References Cited

U.S. PATENT DOCUMENTS 6,113,972 A * 9/2000 Corliss et al. ............... 426/613

* cited by examiner

*Primary Examiner*—Thurman K. Page
*Assistant Examiner*—Marc C. Fitzgerald
(74) *Attorney, Agent, or Firm*—Ladas & Parry LLP (57) ABSTRACT

The invention includes a nonformulated, low-dose hypocholesterolemic composition comprising soya proteins and β-sitosterol, wherein the soya proteins and the β-sitosterol are present in a weight ratio of about 6±1.5 of the soya proteins to about 1±0.2 of the β-sitosterol; and wherein the composition is made up as an optimal daily dose of only the two components for adults or for children.

26 Claims, 3 Drawing Sheets

Figure 1

AHA= American Heart Association Dietary Recommendations
SS= Soya supplemented in sitosterols

HYPOCHOLESTEROLEMIC COMPOSITION AND METHODS OF USE

CLAIM OF BENEFITS OF PROVISIONAL APPLICATION

Applicants claim the benefits of their U.S. Provisional application Ser. No. 60/338,402, filed on 30 Nov. 2001, the contents of which are hereby expressly incorporated herein in their entirety by this reference.

BACKGROUND OF THE INVENTION

1. Field of the Invention

This invention involves a hypocholesterolemic composition for oral administration comprising an association of soya proteins with sitosterols. The soya proteins and the sitosterols may be of natural origin.

The types of vascular damage that can be caused by a hypocholesterolemic condition are numerous; and a balanced diet plays a role of primary importance in the prevention of such alternations. The populations that are more exposed to this type of pathology are the richer ones whose normal everyday diet, apart from being unbalanced, often exceeds daily requirements.

Hypercholesterolemia can be treated either pharmacologically or by undertaking preventative action in terms of modifying or integrating the usual nutritional intake.

The influence of soya proteins on nutrition is observable both in normal cholesterol level and in hypocholesterolemic conditions.

Sitosterols, β-sitosterols in particular, are substances that are used extensively in hypocholesterolemic treatments. Their chemical structure, similar to cholesterol, differs because of an ethyl group bound to the carbon in position 24, provides these substances with an absorption behavior which is very different from that of cholesterol.

These substances, contrary to the cholesterol contained in food, are not absorbed and interfere with the absorption of the cholesterol taken in. The limited food absorption causes a consequent and significant hypocholesterolemic effect.

2. Description of Related Art

GB-A 2 028 341 describes the use of a composition containing soya protein and pectin for reducing cholesterol level. The daily dose is 60–90 g/day soya protein and 1.5–3 g/day pectin.

GB-A 1 427 253 discloses an antilipemic composition comprising a nonsaponifiable fraction of soybean oil, said fraction containing about 45% by weight of plant sterols (campesterol, stigmasterol, and β-sitosterol) and about 20% by weight tocopherols. The use of this fraction allows the user to reduce dramatically the daily dose of sitosterol compared to the prior art. It is shown that 1200–1800 mg/day of this composition significantly lowers the cholesterol level in patients.

In GB-A 1 427 253 the problem is solved or ameliorated by the use of a nonsaponifiable fraction of soybean oil. Although the hypocholesterolemic effect of soya protein is disclosed in GB-A 2 028 341, there is nothing in either GB-A 2 028 341 or in GB-A 1 427 253 that would suggest that soya protein and sitosterols could have a synergistic effect that would lead to a significant decrease in t he daily dose of both compounds.

EP-B 669 835 describes hypocholesterolemic compositions with soya proteins associated synergistically with sitosterol. These compositions contain from 50 mg to 2000 mg of Soya proteins and from 10 mg to 1000 mg of sitosterols per unit, both of natural origin.

SUMMARY OF THE INVENTION

The present invention turns on the synergistic activity of the two hypocholesterolemic substances (soya proteins and sitosterols), which together can lead to a reduction in the daily dose of hypocholesterolemic substances that are used in an hypocholesterolemic diet.

The present invention includes a nonformulated, low-dose hypocholesterolemic composition comprising soy protein(s) and sitosterol(s) (e.g., β-sitosterol). The invention also includes methods of treating hypercholesterolemia using this hypocholesterolemic composition.

The present invention includes a hypocholesterolemic composition comprising soy protein(s) and sitosterol(s) (e.g., β-sitosterol). The weight ratio between the soya proteins and the sitosterols will generally be between about 1:1 and about 10:1. Alternatively, the weight ratio between the soya proteins and the sitosterols may be about 3:1 to about 9.5:1. In another alternative, the weight ratio between the soya proteins and the sitosterols may be about 6:1 or about 4:1; or the hypocholesterolemic composition may have a weight ratio of about 6±1.5 of soya proteins to about 1±0.2 of sitosterols.

The present invention includes a hypocholesterolemic composition comprising soya protein(s) and sitosterol(s), wherein the weight ratio of soya proteins to sitosterols is about 4:1 in a daily dose for adults of about 8±1 g and in a daily dose for children of about 2±0.5 g. Alternatively, the daily dose for children 6–12 years of age may be about 0.13 g. of the hypocholesterolemic composition for each kg. of body weight.

One technical problem that is being solved or ameliorated by the invention according to this current application is lowering the daily dose of sitosterol without decreasing the efficiency of the hypocholesterolemic composition.

DETAILED DESCRIPTION OF THE INVENTION

The hypocholesterolemic composition of the present invention may be used to treat hypercholesterolemia, e.g., moderate and/or chronic hypercholesterolemia in a patient by administering to the patient a daily dose of the hypocholesterolemic composition, which optionally may be dissolved in water/watery drinks or which optionally may be mixed with pasty/solid food, i.e., the soya proteins and the sitosterols are optionally integrated into, mixed with, or dissolved in the patient's food or beverages.

Optionally, there are no other modifications of the patient's diet; or there are no other major or significant modifications of the-patient's diet to treat hypercholesterolemia. Optionally, the soya proteins and the sitosterols are not administered simultaneously to the patient. Optionally, there is a gap between when the soya protein is administered to the patient and when the sitosterol is administered to the patient. The gap may range from about 30, seconds to about 12 hours. Alternatively, the gap may range from about 1 minute to about 8 hours, or about 5 minutes to about 5 hours, or about 10 minutes to about 3 hours, or about 15 minutes to about 2 hours, or about 30 minutes to about 1 hour. Optionally, the patient may eat a meal or a snack between time when the soya protein is administered and the time when the sitosterol is administered.

Optionally, the soya protein is administered before a meal or snack; and the sitosterol is administered during or after a meal or snack. Alternatively, the sitosterol may be administered before a meal or snack; and the soya protein may be administered during or after a meal or snack.

Sitosterols are present in food of vegetable origin, particularly in walnuts, oils and generally in vegetables and fruit with a high lipid content. The human organism and that of mammals in general is unable to synthesize sitosterols and therefore, blood and tissue levels of such substances depend solely on food intake.

The cyclopentanperhydrophenanthrenic structure does not differ from that of cholesterol. Closely related structural similarities are evident also with the sterols of certain types of shellfish, such as 22-dehydrocholesterol, braxycasterol and 24-methylenecholesterol.

Sitosterols intake through food strongly varies from region to region. In the male omnivorous Caucasian adult it is estimated to be between 100 to 400 mg/day, sum of all sitosterols. In the absence of pathologies absorption, however, is minimal, oscillating around 5% of total intake. This is probably correlated with the minor capacity of these instances, compared to cholesterol, to form micelle or pseudomicelle aggregates.

Therefore, sitosterols are assimilated at quantities ranging between 5 and 20 mg/day which must be vehicled through lipoproteins. The remaining amount is generally metabolized in a similar manner to cholesterol: conversion into 5-β-sitosterol or other corresponding catabolites in the intestinal lumen, which in turn are further converted and excreted similarly to coprostanol, a cholesterol derivative.

All sitosterol metabolic processes in the intestinal lumen, however, seem to be slower than the corresponding cholesterol processes, including intestinal mucosa esterification due to CoA dependent esterase. The conversion of sitosterols into biliary acids is also less efficient, only 20% of the sitosterols present in food are converted—i.e.: 1% of the amount assimilated through the daily diet, and slower than cholesterol.

Sitosterols are, however, excreted as such in bile and, when converted into biliary acids, appear to form mainly colic and chenodeoxycholic acid.

Sitosterols intestinal residence times are longer than those of cholesterol. Due to reduced intestinal esterification, however, only ¼ of lymphatic sitosterols are esterified, compared to ¾ of cholesterol, whilst in blood the free/esterified ratio becomes practically identical for both molecule classes because of the lengthy re-circulation times and the constant action of Lecithin Cholesterol Acyl transferase.

The hypocholesterolemic effect of sitosterols depends on their solubility, absorption speed and the sitosterol/cholesterol ratio in the intestinal lumen, and probably also on their minor capacity to penetrate into cellular membranes. The formation of micelle, below that of cholesterol, and their uptake by intestinal microvilli seems to be fundamental in inducing a reduction in cholesterol absorption, which can be significant, although the precise receptor sites where the competition between sitosterols and cholesterol occurs have not yet been identified. The mechanism, however, seems to be competitive, since the effect of the reduced cholesterol absorption appears to be proportional to sitosterol and cholesterol intake during a single meal.

It must, however, be remembered that there are also numerous works which indicate that sitosterols exert a direct regulatory effect on extra-intestinal lipid metabolism, e.g. activity on AcetylCoA carboxylase; activity on LCAT, ACA, 3 MgCoAR, etc. From this point of view, it is interesting to note that sitosterols concentrate in the liver, the adrenal cortex and the gonads much more than cholesterol. In other words the hepatic C/P ratio varies in favor of sitosterols in spite of the minor absorption and bioavailability.

The high concentration of sitosterols in organs rich in LDL-receptors appears to find explanation in the fact that hepatic sitosterol concentrations are high and the liver is or appears to be the organ which incorporates these substances in LDL. In man, sitosterols are found in HDL, but not except for negligible traces in VLDL. Sitosterols could be a "physiological" precursor of cortisol.

Many lamellar-branchial fish, but not crustaceans, contain sterols C26, such as 22-trans-24-norcholesta-5,22-dien-3-β-ole or 24 methylenechole-sterol, 22 dehydrocholesterol or braxycasterol. These compounds are also potentially interesting for the treatment of human pathologies. Such sterols are excreted at ratios higher than those of cholesterol and are specifically transported by all lipoproteins. Whether they are precursors of hormones or biliary acids is unknown. Nevertheless, the human body is able to esterify and transport them in a rather efficient manner.

Phytosterolemia is a genetic disease previously classified among lipid texaurismoses, old non-anglosaxon definition of taxonomy, belonging to the general group of family diseases with deposition of sterols that differ from cholesterol together with cerebrotendinous xanthomatosis. Increased sitosterol absorption could represent the cause.

These diseases are exceptionally rare, at least in terms of extraordinary phenotypes which might be published in literature underestimated bias and are characterized by xanthomatosis and early coronary cardiopathy.

The genetic deficit of phytosterolemia has not yet been identified. The disease appears to be transmitted with a recessive autosomic characteristic and one single gene appears to be responsible which is "strongly" recessive and rare, although polygenic interpretation models have been proposed and certain authors have suggested a possible expression at heterozygote status. This gene might directly or indirectly facilitate assimilation of sitosterols, which seems to represent the primary movements of these diseases, although the interpretation of the etiopathogenesis of the disease based solely on increased absorption does not appear to be completely convincing.

In some of the rare cases described in literature, however, there is clear evidence of increased absorption of sitosterols (and shellfish sterols in some patients) up to 28% (19% and 24% in other patients) of uptake (as opposed to 2–5% that is considered normal).

The cause of the increased absorption might be due to the altered formation of micelle in the intestinal lumen, that could be the consequence of reduced biliary cholesterol outflow which would appear to facilitate solubilization of sitosterol micelle. Reduced intestinal ACAT activity might also facilitate the increased absorption. In some of these patients there is clear evidence of an increase in the half-life of both sitosterol and cholesterol.

Early atheroma in these subjects seems to be correlated with the increased concentration of sitosterol, which would seem to have an atherogenic potential, reasonably those vehicled by LDL, similar to that of cholesterol.

Accumulation of sitosterol in lipoproteins could be further facilitated by their scarce conversion in biliary acids. In addition, during phytosterolemia cholestanol is also accumulated, as in cerebrotendinous xanthomatosis (XCT), but due to increased absorption and not, as in XCT, to increased conversion by the precursors which do not "mature" along the physiological biliary acid formation route consequent to the hepatic 26-hydroxylase deficit.

An increased concentration of sitosterols in red blood cell cellular membranes could be the cause of increased red blood cell fragility and, therefore, possibly the hemolytic syndromes described in certain patients.

Tendinous xanthomas, Achilles tendon and other sites, infrequent xanthelasmas, sporadic gerontoxon. Appearance of skin manifestations in children or young adults. Early coronary and extra-coronary atheroma, with fatal IMA during adolescence or adulthood in the male. It is difficult to evaluate early coronary atheroma in females. Episodes of acute or chronic hemolytic anemia have been reported. Hypersplenism and platelet abnormalities are often present. Arthralgia and polyarthralgia are rare and might, in any case, have a similar pathogenesis to that of FH.

Hypercholesterolemia is not always present, whilst there is recurrent evidence of an increase in sitosterol (1 mg/dL n.v.; max. in normal children on a vegetable oil diet: 9–10 mg/dL; up to 70 mg/dL in probands).

The plasma concentrations of the other vegetable sterols, as well as those of cholestanol and, sometimes, shellfish sterols are also increased, the latter by a factor of 5–10: n.v. 1–2 mg/dL, proband values up to 20 mg/dL. The sitosterol/cholesterol ratio in red blood cell membranes is also increased.

In xanthomas sitosterols represent 15–25% (not the totality) of sterols, which demonstrates the role played by LDL cholesterol in these patients. The bile of these patients contains mainly C24 (colic and chenodeoxycholic) biliary acids with sub-saturated bile, compared to cholesterol. (NB: in normal subjects sitosterol and shellfish sterols are excreted in the bile as such). Excretion of neutral fecal sterols is low.

The disease may be treated with an exclusion diet and with cholestyramine. The prognosis, however, is serious.

Assuming the genetic deficit is always rare (or rather, that in the population there are no, as is vice versa possible, clusters of subjects with sterol absorption above 5% ) and that the influencing environmental factors (food, infections, iatrogenic, etc.) are very modest, the oral sitosterol dose that could be potentially harmful in chronic subjects is presumably around 1000–1250 mg/day, or in any case a dose that increases sitosterolemia above a limit that is between 1 and 5 mg/dL.

Vice versa, in a population with supposedly highly heterogeneous patterns in relation to sitosterol absorption, the above doses should be decreased.

The basic problem is that sitosterols and shellfish sterols above certain threshold levels, which in normal human nutrition are probably hardly ever reached, appear to be potentially atherogenic similarly to cholesterol. There is little knowledge on their athero-thrombogenic potential in oxidated forms.

If this is so, only a hypocholesterolemic action which causes no increase whatsoever in sitosterol plasma or tissue levels could be considered useful.

The first essential step to be taken for the verification of the safety of a product based on sitosterol is the daily dose (and re-distribution) in lipoprotein fractions during therapy. If the LDL-cholesterol level is reduced, without significant variations of LDL or greater formation of oxidized compounds and, if the result is maintained in the short as well as long-term, the product can be considered safe, in spite of the mere extrapolations indicated by the pathology.

The subsequent step could include evaluation of the effect of a regular daily does compared to a dosage adapted by the patient, on a daily basis, in relation to the actual diet.

The present invention also includes a method for treating high hypercholesterolemia by using the hypocholesterolemic composition as a coadjuvant during drug treatment.

The compositions which are the subject of the invention may also contain active principles or integrators with coadjuvant, complementary, or useful activity. Examples of these elements which can be usefully employed for the purpose are: minerals, salts, vitamins, digestive enzymes, soluble fibers, insoluble fibers, amino acids, phospholipids, etc.

The compositions which are the subject of the invention are prepared using traditional techniques and excipients. These compositions are prepared by mixing soya proteins and sitosterols with excipients that are physiologically suitable and with pleasant appearance, color, and flavor. Among the excipients available for alimentary use are diluting agents, sweeteners, binding agents, flavoring agents, lubricants, antiaggregating agents, natural and synthetic coloring agents, solubilizers, surfactants, preservatives, etc.

Examples of diluting substances are: microcrystalline cellulose, lactose, glycine, rice starch, saccharose, fructose, sorbitol, etc.; examples of binding agents are: starch water, pvp, methylcellulose, etc.; examples of flavoring agents are: citric acid, tartaric acid, sodium chloride, sodium glutamate, menthol, etc.; examples of lubricants are: PEG, magnesium stearate, stearic acid, talc, etc.

The examples of dietary compositions include: chewable, effervescent, swallowable, and coated tablets, film-coated pills, capsules, soft gelatin capsules, syrup, fruit beverages, granule sachets, fruit gelatins, sweets, etc. The following are hypocholesterolemic dietary formulations:

| Nucleus: | Amount |
| --- | --- |
| Coated Tablets | |
| Soya proteins | 500 mg |
| sitosterols | 100 mg |
| lactose | 90 mg |
| magnesium stearate | 10 mg |
| Coating: | |
| Methylcellulose | 10 mg |
| titanium dioxide | 2 mg |
| PEG 6000 | 3 mg |
| talc | 5 mg |
| Tablets | |
| Soya proteins | 300 mg |
| sitosterols | 200 mg |
| maize starch | 30 mg |
| pvp | 20 mg |
| lactose | 50 mg |
| talc | 10 mg |
| magnesium stearate | 5 mg |
| Granules for extemporaneous suspension | |
| Soya proteins | 800 mg |
| sitosterols | 200 mg |

-continued

| Nucleus: | Amount |
|---|---|
| saccharose | 2000 mg |
| sodium saccharinate | 20 mg |
| apple flavoring | 50 mg |
| Capsules: | |
| Soya proteins | 100 mg |
| sitosterols | 100 mg |
| magnesium stearate | 10 mg |
| silica precipitate | 5 mg |
| Shell: | |
| gelatin | 100 mg |
| Chewable tablets | |
| Soya proteins | 300 mg |
| sitosterols | 200 mg |
| mannitol | 500 mg |
| pvp | 20 mg |
| sorbitol | 100 mg |
| aspartame | 3 mg |
| magnesium stearate | 5 mg |

The dietary preparation based on soya proteins/sitosterols can be associated with substances such as food fibers (soluble or insoluble) to produce dietary hypocholesterolemic-bulking agents. The following is an example of a hypocholesterolemic-bulking agent:

| Granules for extemporaneous suspension | |
|---|---|
| Soya proteins | 800 mg |
| sitosterols | 200 mg |
| guar gum | 2000 mg |
| saccharose | 1000 mg |
| sodium saccharinate | 20 mg |
| orange flavoring | 50 mg |

The hypocholesterolemic association combined with enzymes of vegetable origin such as bromelain gives hypocholesterolemic-digestive products. The following is an example of a formulation for a hypocholesterolemic-digestive product:

| Chewable tablets | |
|---|---|
| Soya proteins | 300 mg |
| sitosterols | 200 mg |
| bromelain | 10 mg |
| mannitol | 500 Mg |
| PVP | 20 mg |
| sorbitol | 100 mg |
| aspartame | 3 mg |
| magnesium stearate | 5 mg |

The hypocholesterolemic composition may comprise soya proteins associated synergistically with sitosterol, wherein the composition contains from about 50 mg to about 2000 mg of soya proteins and from about 10 mg to about 1000 mg of sitosterols per unit. The soya proteins and the sitosterols optionally may be of natural origin. The hypocholesterolemic composition may contain other active principles or integrators with a coadjuvant, complementary, or useful activity. The hypocholesterolemic composition also may contain at least one substance chosen from the group consisting of: mineral salts, vitamins, digestive enzymes, soluble fibers, insoluble fibers, amino acids, and phospholipids. The hypocholesterolemic composition may be in the form of chewable, effervescent, swallowable and coated tablets, capsules, soft gelatin capsules, syrup, fruit beverages, granule sachets, fruit gelatins, or sweets.

The characteristic data of α-sitosterol, β-sitosterol, and γ-sitosterol are as follows.

α-sitosterol: 4-Methylstigmasta-7,24(28)-dien-3-ol, ($C_{30}H_{50}O$),

β-sitosterol: Stigmast-5-en-ol, ($C_{29}H_{50}$),

γ-sitosterol: (24S)-Stigmast-5-en-3β-ol, ($C_{29}H_{50}O$).

The inventors have tested the synergistic effect of soybean proteins and β-sitosterol on plasma lipid level of normolipidemic and moderately hypocholesterolemic subjects.

The aim is to verify the efficacy as antihypercholesterolemic agent of a new low-dose formulation of soy bean proteins supplemented in β-sitosterol in moderately hypocholesterolemic subjects. In the first phase, it has been observed that the association of soy bean proteins and β-sitosterol determined a significantly greater decrease in plasma TC, LDL-C, VLDL and TG. Than the sum of the effects of the single components in normocholesterolemic subjects, even if the effect amplitude is maybe greater than that obtainable after a longer stabilisation.

In the second phase, the administration of only 4 g/day of soy bean proteins added in β-sitosterol determined a 15.3%, 22.26%, 26.41%, 34.83% mean decrease respectively in TC and LDL-C plasma concentrations and in TC/HDL-C and LDL-C/HDL-C risk ratios. On the other side, it determined a 15.28% mean increase in HDL-C plasma concentrations without significant change in TG plasma level (−2.24%).

The very low product dose necessary to obtain the observed results has the advantage to not unbalance the daily dietary intake of proteins in rapport to the other nutrients and it not implies a significant modification of the dietary habitude pattern. This last factor is especially important to obtain a good patient compliance to the chronic treatment, that is necessary for achieve the desired clinical outcomes.

The inventors interest has been especially focused on sitosterols, as cholesterol lowering agents in foods. Sitosterols, made up of plant sterols and their chemically modified derivatives, have found a place in the growing spectrum of "functional foods" or "nutraceuticals" in a number of countries. Nevertheless, sitosterols, as of September 2000, have received health clam from the United States Food and Drug Administrations. Key current issues surrounding use of plant sterols and their derivatives are relative efficacy of different mixtures and long-term safety, while efficacy and short-term safety have been established in many previous and recent studies. In a meta-analyses it was estimated that after adjustment for initial serum cholesterol concentrations and other variables, the ingestion of 25 or 50 g of soy proteins per day was estimated to decrease serum cholesterol levels by 8.9 or 17.4 mg per decilitre respectively, independently from the soybean or sitosterols mixture formulation. In particular ingestion of soy protein achieved an average 9.3% decrease in plasma Total Cholesterol (TC), a 12.9% decrease in Low Density Lipoprotein Cholesterol (LDL-C), and a 10.5% decrease in Triglycerides (TG) and a non significant 2.4% increase in High Density Lipoprotein Cholesterol (HDL-C) plasma levels. Moreover, persons with moderate or severe hypercholesterolemia (>250 mg per decilitre) should have even larger decreases in serum cholesterol concentrations when soy protein replaces animal protein in the diet. Even if some studies have demonstrated that phytostanols (saturated plant sterols, potent inhibitors of bowel cholesterol absorption) are cholesterol lowering agents more effective than sitosterols, most recently it has been shown that all current soy bean derived mixtures are more or less equivalent in their cholesterol lowering ability. The major difference is still the quantity of product to daily take to achieve similar results, ranging in different studies from 18 g to 124 g. The aim is to verify the efficacy as plasma cholesterol lowering agent of a new low-dose formulation of soy bean proteins supplemented in β-sitosterol both in normocholesterolemic and dyslipidaemic subjects.

The mechanism and component of soy responsible has not been fully established.

Most Authors suggest that feeding intact soy protein impairs cholesterol absorption and/or bile acid re-absorption, however these data have not clearly confirmed in humans. The metabolic changes that have been observed on soy protein feeding in a variety of animal models, and in some cases humans, include increased cholesterol synthesis, increased bile acid synthesis (or faecal bile acid excretion), increased apoB or E receptor activity and decreased hepatic lipoprotein secretion and cholesterol content, which are associated with an increased clearance of cholesterol from the blood. Amino acid composition or proportionality of soy could cause changes in cholesterol metabolism. Others have proposed that non protein components associated with soy protein affect cholesterol metabolism either directly or indirectly. In particular, soy phytoestrogens, acting as selective oestrogen receptor modulators, may account for most part of the antihypercholesterolemic effects of soy protein.

Whereas the cholesterol-lowering effect of plant sterols has been established some decades ago, more recent results produced new information concerning relative efficacy of various mixtures and dose-response relationships. Especially, it has been demonstrated that a low supplementation in sitosterols is sufficient to significantly lower plasma cholesterol concentrations both in normocholesterolemic and hypocholesterolemic subjects. Even the antihypercholesterolemic activity of isolated β-sitosterol has been clearly demonstrated, it is more and more investigated for his property to improve urinary symptoms and flow measures in benign prostate hypertrophy affected patients.

Main advantages of a low-dose soy bean protein formulation are, among the others, two: it does not unbalance the daily energy intake toward proteins nor implies a significant modification of the dietary habitude pattern. This last factor is especially important to obtain a good patient compliance to the chronic treatment, that is necessary for achieve the desired clinical outcomes.

In the first phase, the inventors observed that the association of soy bean proteins and β-sitosterol determined a significantly greater decrease in plasma TC, LDL-C, VLDL and TG than the sum of the effects of the single components in normocholesterolemic subjects, even if the effect amplitude is maybe greater than that obtainable after a longer stabilisation.

In the second phase, the administration of only 4 g/day of soy bean proteins added in β-sitosterol determined a 15.3%, 22.26%, 26.41%, 34.83% mean decrease respectively in TC and LDL-C plasma concentrations and in TC/HDL-C and LDL-C/HDL-C risk ratios. On the other side, it determined a 15.28% mean increase in HDL-C plasma concentrations without significant change in TG plasma level (−2.24%). One more time, the amplitude of the observed effect could be greater than expected on more strictly selected patients because of increased dietary cholesterol adsorption inhibition effect (we are planning an experience on selected patients affected by multigenic hypercholesterolemia and because of it constantly submitted to a diet poor in cholesterol).

Beyond its cholesterol lowering effect, the very low quantity administered has the advantage to not unbalance the daily dietary intake of proteins in rapport to the other nutrients (as observed from the patient bromatological pattern), while the chosen rapport between mixed soy derived protein and β-sitosterol is that at highest solubility both in lipids and in water.

Even the US FDA recommends including four servings of at least 6.25 g each (25 g/day) of soy protein into a diet low in saturated fat and cholesterol to reduce the risk of heart disease. However, the soy pills and isolated supplements such as isoflavones are not recommended (Dunn, 2000). Moreover, it has been estimated (but still not demonstrated) that a 2 g of plant sterols could be expected to reduce the risk of coronary heart disease by 25%. According to this recommends, low doses of soy bran protein added in β-sitosterol seems to be a practical and safe alternative for patients seeking modest reductions in LDL-C (<15%). Although the use of soy alone may not allow patients with hyperlipidemia to achieve target lipid parameters, as indicated by the more recent Guidelines for Coronary Heart Disease prevention, they don't pharmacologically interact with lipid lowering therapy. On the contrary, the co-assumption of soy bean protein and a statin seems to improve the cholesterol lowering effect of the drug.

Further double-blind randomised clinical trials on wider population samples have to be carried out to better evaluate the real therapeutic gain obtaining from the use of this formulation in rapport to a low fat diet and, eventually, in association of a lipid lowering drug.

The inventors have further tested the synergistic effect of a new low-dose formulation of soy bean protein supplemented in β-sitosterol on plasma lipid level of moderately hypocholesterolemic subjects.

Soyfoods have received widespread attention during the past five years for their role in disease prevention, especially in relation to coronary heart disease, osteoporosis, cancer and, even less, renal diseases. The interest of the researchers has been especially focused on sitosterols, as cholesterol lowering agents in foods. Sitosterols, made up of plant sterols and their chemically modified derivatives, have found a place in the growing spectrum of "functional foods" or "nutraceuticals" in a number of countries. Nevertheless, sitosterols, as of September 2000, have received health claim from the United States Food and Drug Administrations. Key current issues surrounding use of plant sterols and their derivatives are relative efficacy of different mixtures and long-term safety, while efficacy and short-term safety have been established in many previous and recent studies. In a meta-analyses it was estimated that after adjustment for initial serum cholesterol concentrations and other variables, the ingestion of 25 or 50 g of soy protein per day was estimated to decrease serum cholesterol levels by 8.9 or 17.4 mg per decilitre respectively, independently from the soybean or sitosterols mixture formulation. In particular ingestion of soy protein achieved an average 9.3% decrease in plasma Total Cholesterol (TC), a 12.9% decrease in Low Density Lipoprotein Cholesterol (LDL-C), and a 10.5% decrease in Triglycerides (TG) and a non significant 2.4% increase in High Density Lipoprotein Cholesterol (HDL-C) plasma levels. Moreover, persons with moderate or severe hypercholesterolemia (>250 mg per decilitre) should have even larger decreases in serum cholesterol concentrations when soy protein replaces animal protein in the diet. Even if some studies have demonstrated that phytostanols (saturated plant sterols, potent inhibitors of bowel cholesterol absorption) are cholesterol lowering agents more effective than sitosterols, most recent findings support the conclusions of Anderson and colleagues that all current soy bean derived mixtures are more or less equivalent in their cholesterol lowering ability. The major difference is still the quantity of product to daily take to achieve similar results, ranging in different studies from 18 g to 124 g.

The aim is to verify the efficacy as plasma cholesterol lowering agent of a new low-dose formulation of soy bean proteins supplemented in β-sitosterol in moderately hypocholesterolemic subjects.

A large body of literature indicates that proteins from soybeans reduce blood cholesterol concentrations in experimental animals as well as in humans. The mechanism and component of soy responsible has not been fully established. Most Authors suggest that feeding intact soy protein impairs cholesterol absorption and/or bile acid re-absorption, however these data have not clearly confirmed in humans. Others propose that changes in endocrine status, such as alteration in insulin:glucagon ratio and thyroid hormone concentrations, are responsible. The metabolic changes that have been observed on soy protein feeding in a variety of animal models, and in some cases humans, include increased cholesterol synthesis, increased bile acid synthesis (or fecal bile acid excretion), increased apoB or E receptor activity and decreased hepatic lipoprotein secretion and cholesterol content, which are associated with an increased clearance of cholesterol from the blood. Amino acid composition or proportionality of soy could cause changes in cholesterol metabolism (possibly via the endocrine system). Others have proposed that non-protein components (such as saponins, fiber, phytic acid and isoflavones) associated with soy protein affect cholesterol metabolism either directly or indirectly. In particular, soy phytoestrogens, acting as selective oestrogen receptor modulators, may account for most part of the hypocholesterolemic effects of soy protein.

Whereas the cholesterol-lowering effect of plant sterols was established some decades ago, more recent results produced new information concerning relative efficacy of various mixtures and dose-response relationships. Especially, it has been demonstrated that a low supplementation in sitosterols is sufficient to significantly lower plasma cholesterol concentrations both in normocholesterolemic and hypercholesterolemic subjects. Even the antihypercholesterolemic activity of isolated β-sitosterol has been clearly demonstrated, it is more and more investigated for his property to improve urinary symptoms and flow measures in benign prostate hypertrophy affected patients.

Main advantages of a low-dose soy bean protein formulation are, among the others, two: it does not unbalance the daily energy intake toward proteins nor implies a significant modification of the dietary habitude pattern. This last factor is especially important to obtain a good patient compliance to the chronic treatment, that is necessary for achieve the desired clinical outcomes.

The good results have been obtained with the oral administration of only 10 g/day of soy bean proteins supplemented in β-sitosterol. This very low quantity has the advantage to not unbalance the daily dietary intake of proteins in rapport to the other nutrients, while the chosen rapport between mixed soy derived protein and β-sitosterol is that at highest solubility both in lipids and in water.

Even the US FDA recommends including four servings of at least 6.25 g each (25 g/day) of soy protein into a diet low in saturated fat and cholesterol to reduce the risk of heart disease. However, the soy pills and isolated supplements such as isoflavone are not recommended. Moreover, it has been estimated (but still not demonstrated) that a 2 gr of plant sterols could be expected to reduce the risk of coronary heart disease by 25% (37). According to this recommends, low doses of soy bran protein added in β-sitosterol seems to be a practical and safe alternative for patients seeking modest reductions in LDL-C (<15%). Although the use of soy alone may not allow patients with hyperlipidemia to achieve target lipid parameters, as indicated by the more recent Guidelines for Coronary Heart Disease prevention, they don't pharmacologically interact with lipid lowering therapy. On the contrary, the co-assumption of soy bean protein and a statin seems to improve the cholesterol lowering effect of the drug.

Further double-blind randomised clinical trials on wider population samples have to be carried out to better evaluate the real therapeutic gain obtaining from the use of this formulation in rapport to a low fat diet and, eventually, in association of a lipid lowering drug.

The addition of a low quantity of soy bean proteins supplemented in β-sitosterol (10 g daily or less) to a correct diet could improve the cholesterolemia control in moderately hypercholesterolemic subjects, without significantly modify their daily protein intake and dietary pattern. It could be especially useful to obtain a greater compliance of the patients to the treatment.

The Invention will be further described in Examples in more detail but not exclusively.

EXAMPLES

The chemical analysis of β-sitosterol, which may be used in the present invention is shown in the following table:

Analysis of β-sitosterol: 2.00 kg

| Characteristics | Results [%] | Specifications [%] Minimum | Specifications [%] Maximum | Methods |
|---|---|---|---|---|
| Campesterol | 9.3 | | 10.0 | DRT 1210 |
| Campestanol | 1.2 | | 2.0 | DRT 1210 |
| β-sitosterol | 75.4 | 75.0 | | DRT 1210 |
| β-sitostanol | 11.6 | 10.0 | | DRT 1210 |
| others | 2.5 | | 2.5 | DRT 1210 |
| Weight loss on drying | 0.5 | | 3.5 | DRT 4690 |

The chemical analysis of soya proteins, which may be used in the present invention, is shown in the following table (soya proteine isolated 90% gmo-free type H).

| analytical data | proteins | min 90% |
|---|---|---|
| | moist | max 6.0% |
| | ashes | max 6.5% |
| | fat | max 1% |
| | fiber | max 0.5% |
| | PH | 6,5–7,5 |
| arsenic (AS) | max 0.5 ppm | |
| lead (Pb) | max 1 ppm | |
| total microbic amount | max 10.000 CFU/g | |
| salmonell: | absent in 25 g | |
| E. Coli: | absent in 1 g | |

The Inventors have tested the effects of the new low-dose formulation of soy-bean protein supplemented in β-sitosterol on plasma lipid level of moderately hypercholesterolemic subjects. The following is an Executive Summary of the Third Report of the National Cholesterol Education Program (NCEP) Expert PLanel on Detection, Evaluation, and Treatment of High Blood Cholesterol in Adults (Adult Treatment Panel).

| ATP III Classification of LDL, Total, and HDL Cholesterol (mg/dL)* | |
|---|---|
| LDL cholesterol | |
| <100 | Optimal |
| 100–129 | Near or above optimal |
| 130–159 | Borderline high |
| 160–189 | High |
| ≧190 | Very high |
| Total cholesterol | |
| <200 | Desirable |
| 200–239 | Borderline high |
| ≧240 | High |
| HDL cholesterol | |
| <40 | Low |
| >60 | High |

*ATP indicates Adult Treatment Panel; LDL low-density lipoprotein; and HDL high density lipoprotein Example 1

Synergistic Effect of Soy Bean Proteins and β-sitosterol on Plasma Lipid Level of Normolipidemic and Moderately Hypercholesterolemic Subjects For the first phase, 18 normocholesterolemic healthy male subjects (mean age: 32.5±8 years) have been enrolled. All subjects followed a stabilisation diet period of seven days during which they received some advises concerning their nourishment (according to the American Heart Association recommends), without any radical modification of their diet customs. A dietician monitored the patient dietary pattern trough the "Seven days questionnaire" for all the experimental duration. Patients were imposed to stop any nutritional supplementation. After this period, all subjects ingested for fifteen days 400 mg β-sitosterol two times/day (6 subjects), 1600 mg soy bean proteins two times/day (6 subjects) or a low dosage product containing soy proteins supplemented in β-sitosterol in a rapport 4:1 (offered and patented by Inpharma SA, Lugano, Switzerland), 2 g two times/day (6 subjects).

For the second phase, 15 hypercholesterolemic male subjects (mean plasma LDL-C level=172±12 mg/dL ranging from 160 to 190 mg/dL) have been enrolled (mean age: 37.8±9.1 years). After a similar fifteen days stabilisation diet period, they ingested 10 mg one time/day of the tested product for 15 days. At each stage of both experimental phases a complete plasma lipid and lipoprotein assessment has been carried out.

The hematochemistry measurements have been carried out on venous blood coming from antecubital harm vein, after 12 fasting hours after the stabilisation diet period and at the end. Blood has been collected into tubes not containing heparin or other anticoagulant, plasma was immediately separated by high-speed centrifugation at 3500×g for twenty minutes. TC, HDL-C, TG, Glucose, and Uric acid have been determined with standardised enzymatic calorimetric methods (Gaddi et al., 2001). LDL-C plasma level has been estimated with the Friedewald's formula [LDL-C=TC-(TG/5+HDL-C)], for TG<350 mg/dL.

Data have been sampled in a specific database and analysed with the help of the SPSS 8.0 statistical software. A normality Shapiro-Wilks test has been carried out on all the tested variables, followed by ANOVA and two-tails t-test for paired samples, when possible, and by a post-hoc Tukey's test. Percentages have been compared with the Fisher's exact test. Correlation degree between baseline plasma lipid levels and reduction obtained with the treatment were estimated with a Pearson's bivariate correlation test followed by linear regression. For all tests a "p" level less than 0.05 has been considered as significant.

Peripheral systolic and diastolic blood pressure, BMI, basal glucose, uric acid and fibrinogenemia did not significantly change during the various observation periods. The bromatological pattern did not significantly change after the dietary stabilisation period, as well. The main results of the first experimental phase are resumed in table 1.

TABLE 1 shows plasma lipoprotein variations induced by different low dose soya components and its association

| Laboratory variable | 3200 mg Soy bean proteins | 800 mg β-sitosterol | Combination |
|---|---|---|---|
| Total Cholesterol | −5.3% | −3.2% | −16.2%* |
| Low Density Lipoproteins | −8.1%* | −4.9% | −18.3%* |
| High Density Lipoproteins | +0.5% | +0.3% | +0.6% |
| Very Low Density Lipoproteins | −4.2% | −0.2% | −15.4%* |
| Tryglycerides | −4.0% | −0.1% | −16.9%* |
| Apolipoprotein B | −2.0% | −0.3% | −6.5% |
| Apolipoprotein AI | −0.4% | −0.1% | −4.1% |

*= P < 0.05 in rapport to post-seven days of stabilisation diet values

In the second experimental phase, from the end of the stabilization diet period to the end of the soybean proteins added in β-sitosterol supplementation we observed a 34.9±23.6 mg/dL, 39.8±26.72 mg/dL, 5.1±13.99 mg/dL, 1.87±1.53 and 39.8±26.72 mean decrease in respectively plasma TC (t=−4.68, 14DF, p=0.01), LDL-C (t=−4.71, 14DF, p=0.01), TG (t=−1.15, 14DF, p=0.279), TC/HDL risk ratio (t=−3.86, 14DF, p=0.004) and LDL-C/HDL-C risk ratio (t=−3.86, 14DF, p=0.004), associated with a 5.9±5.56 mg/dL mean increase in HDL-C (t=2.85, 14DF, p=0.019) plasma concentrations.

Figure 1:
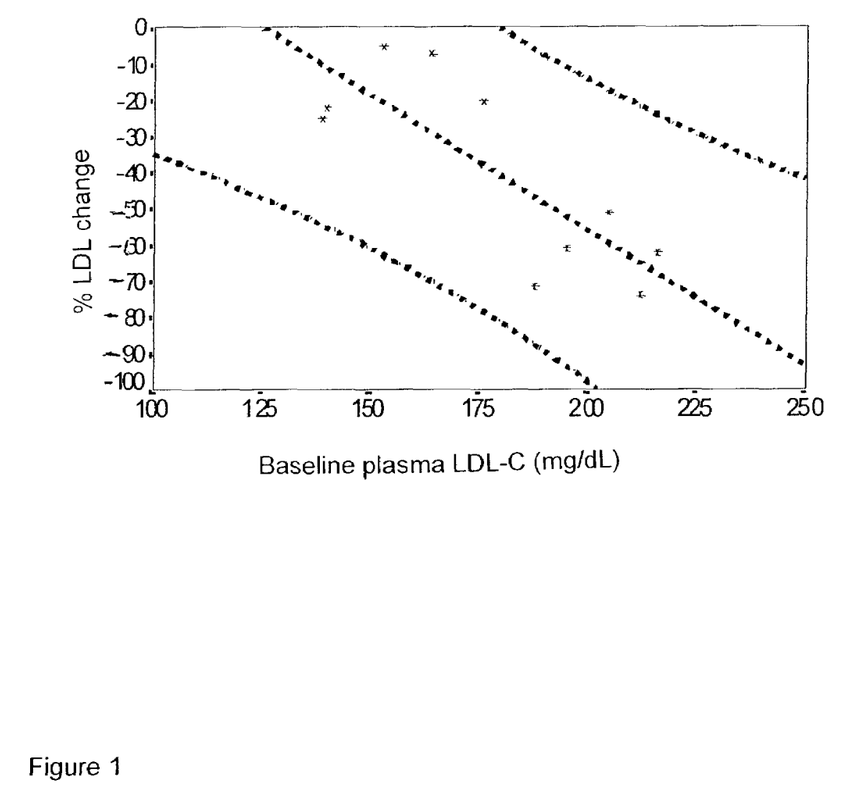
FIG. 1 shows the linear regression between LDL-C (Low Density Lipoprotein Cholesterol) plasma value at the end of the stabilisation diet period and the LDL-C variation obtained at the end of the treatment period.

A positive and statistically significant correlation was observed between the LDL-C measured the end of the stabilization diet period and relative change induced by the soy proteins added in β-sitosterol supplementation (c.c. 0.8071, p=0.005). A similar result was obtained for plasma TC (c.c. 0.8596, p=0.001) level and for TC/HDL-C (c.c. 0.9088, p<0.001) and LDL-C/HDL-C (c.c. 0.7376, p=0.015) risk ratios. The total and mean (95% IC) LDL-C−DLDL-C fit line is reported in FIG. 1. FIG. 1 shows the linear regression between LDL-C plasma value at the end of the stabilisation diet period and the LDL-C variation obtained at the end of the treatment period.

Example 2

Synergistic Effect of a New Low-Dose Formulation of Soy Bean Protein Supplemented in β-Sitosterol on Plasma Lipid Level of Moderately Hypercholesterolemic Subjects Twenty Caucasian patients (M:F=1:1; mean age=50±11 years) affected by type IIa hypercholesterolemia by Fredrickson's classification have been recruited from the Atherosclerosis Center of the University of Bologna (Italy). All subjects have been submitted to a careful medical visit and laboratory analyses aimed at confirming or checking the diagnosis of multigenic type IIa hypercholesterolemia were carried out. Selection criteria were:

LDL-C ranging from 160 to 190 mg/dL (calculated with the Friedewald's formula);

HDL-C>30 mg/dL and TG<200 mg/dL (To convert mg/dL cholesterol to mmol/L, multiply mg/dL by 0.026. Cholesterol of 200 mg/dL=5.2 mmol/L. To convert mg/dL triglycerides to mmol/L, multiply mg/dL by 0.011. Triglycerides of 200 mg/dL=2.2 mmol/L);

No history of cardiovascular disease (myocardial, angina pectoris, stroke, or revascularization);

Absence of diagnosed diabetes mellitus, Familial Combined Hyperlipoproteinemia and X-metabolic syndrome (Reaven's Syndrome) or secondary dyslipidemias and of any disease or treatment that could affect lipid measurements (including steroids, immunosuppressors, perhexilin, Nicotinic acid>50 mg pro die, Plantago psyllium derived products, lipid lowering drugs) or limit the individual's ability to participate (for example endocrine diseases, acute and chronic infections);

Absence of significant abnormalities of laboratory values defined as plasma transaminases concentrations (AST, ALT)>1,5 time of normality superior limit (NSL); Plasma CPK concentrations>2×NSL not explained in other way (for example intense massage or exercise); Hyperuricemia (Uric Acid>7 mg/dL).

after 12 fasting hours. Blood was collected into tubes not containing heparin or other anticoagulant, plasma has been immediately separated by high-speed centrifugation at 3500×g for twenty minutes. TC, HDL-C, TG, Glucose, and Uric acid have been determined with standardised enzimatic calorimetric methods (22). LDL-C plasma level has been estimated with the Friedewald's formula [LDL-C=TC−(TG/5+HDL-C)], for TG<350 mg/dL. For higher TG values, an LDL separation by preparative centrifugation and successive measurement of lipoproteic fraction has been carried out. Apolipoprotein AI and B100 (Apo A1 and ApoB) and fibrinogen have been dosed by immunoturbidimetry as elsewhere described.

Statistical Analyses

Data have been sampled in a specific database and analysed with the help of the SPSS 6.1.2 (Release date: Mar. 24, 1995 statistical software. A normality Shapiro-Wilks test has been carried out on all the tested variables, followed, when possible, by one-way ANOVA, two-tails t-test for paired samples and Tukey's post-hoc test. Percentages have been compared with the Fisher exact test. Correlation degree between baseline plasma lipid levels and reduction obtained with the treatment were estimated with a Pearson's bivariate correlation test followed by linear regression. For all tests a "p" level less than 0.05 has been considered as significant.

Peripheral systolic and diastolic blood pressure, BMI, basal glucose, uric acid and fibrinogenemia did not significantly change during the various observation periods. The bromatological pattern did not significantly change after the dietary stabilisation period, as well. The main results of this experiment are reported in Table 2. Table 2 shows Plasma lipid parameters (mg/dL) at various stages.

|  | Baseline | Stabilization Diet | Soy Protein in β-Sitosterol | After 40 days without Soy supplementation |
|---|---|---|---|---|
| TC | 268.17 ± 19.04 | 257.50 ± 15.77 | 243.08 ± 21.33 | 253.08 ± 26.39 |
| LDL-C | 183.72 ± 20.24 | 169.17 ± 15.3 | 151.93 ± 18.28* | 163.15 ± 24.91 |
| HDL-C | 58.50 ± 16.53 | 55.75 ± 13.15 | 60.33 ± 12.70 | 57.67 ± 16.05 |
| TG | 117.00 ± 49.65 | 162.58 ± 59.72 | 154.08 ± 67.14 | 161.33 ± 65.70 |
| Apo A | — | 117.58 ± 19.02 | 118.67 ± 19.65 | 121.67 ± 15.06 |
| Apo B | — | 118.67 ± 12.28 | 112.00 ± 12.87 | 112.67 ± 14.28 |
| TC/HDL-C | 4.84 ± 1.46 | 4.89 ± 1.35 | 4.26 ± 1.29* | 4.86 ± 1.81 |
| LDL-C/HDL-C | 3.43 ± 1.19 | 3.22 ± 1.00 | 2.68 ± 1.00* | 3.13 ± 1.36 |

*= Significant difference in rapport to stabilization diet

Figure 2:
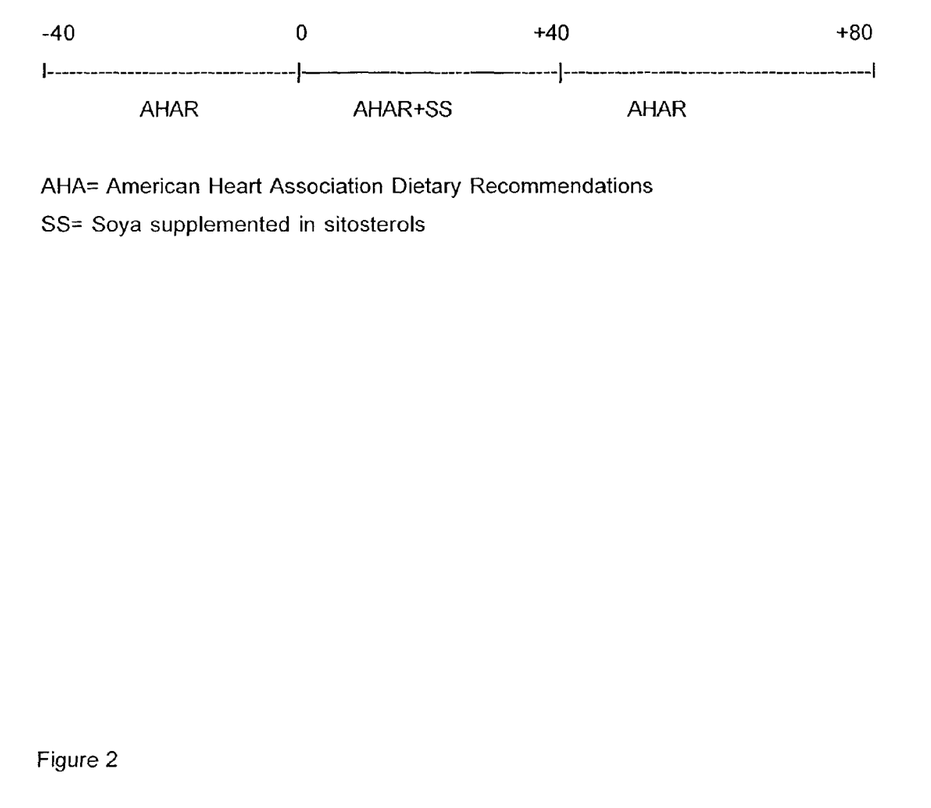
FIG. 2 shows a design of an experimental study

All patients followed a stabilisation diet period of forty days during which they received some advises concerning their nourishment (according to the American Heart Association recommends), without any radical modification of their diet customs. A dietician monitored the patient dietary pattern trough the "Seven days questionnaire" for all the experimental duration. Patients were imposed to stop any nutritional supplementation. After this period, all subjects ingested for forty days a low dosage product containing soy proteins supplemented in β-sitosterol in a rapport 4:1 (Registered and offered by Inpharma SA, Lugano, Switzerland), 10 g one time at day. Then, the patients interrupted ingestion of product with soy protein and β-sitosterol and have been followed up for other forty days of wash out period (FIG. 2). At each experimental stage a complete plasma lipid and lipoprotein assessment has been carried out.

The hematochemistry measurements have been carried out on venous blood coming from antecubital harm vein, From the end of the stabilization diet period to the end of the soybean protein added in β-sitosterol supplementation we observed a 14.42±26.90 mg/dL, 17.23±22.73 mg/dL, 8.50±56.26 mg/dL and 6.67±16.90 mg/dL mean decrease in respectively TC (t=1.86, 19DF, p=0.90), LDL-C (t=2.63, 19DF, p=0.024), TG (t=1 0.52, 19DF, p=0.611) and apo B (t=1.37, 19DF, p=0.199) levels, associated with a 4.58±9.63 and 1.08±19.51 mg/dL mean increase respectively in HDL-C (t=−1.65, p=0.128) and apo A (t=0.019, 11DF, p=0.851) plasma concentrations. That is like to say that the tested treatment induced a mean 5.6% , 10.18% , 5.23% and 5.62% reduction respectively of TC, LDL-C, TG and apo B levels and a mean 8.21% and 0.92% increase respectively in HDL-C and apo A plasma concentrations. Both calculated cholesterol risk ratios decreased significantly (p<0.05).

Figure 3:
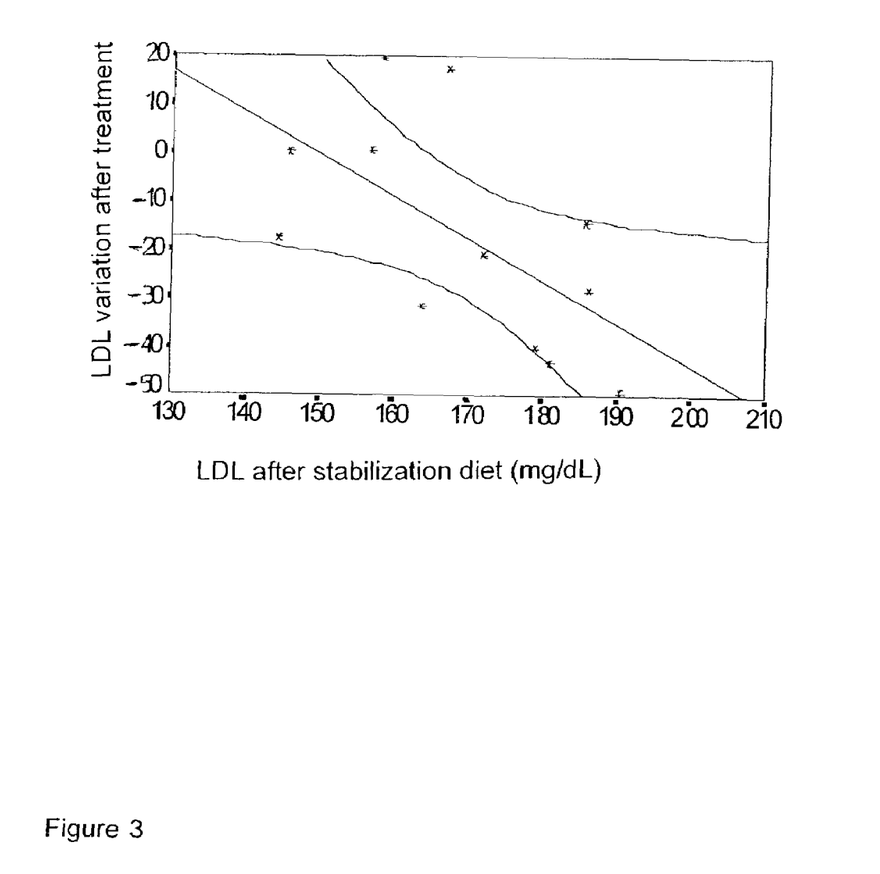
FIG. 3 shows the linear regression between LDL-C (Low Density Lipoprotein Cholesterol) plasma value at the end of the stabilisation diet period and the LDL-C variation obtained at the end of the treatment period.

A positive and statistically significant correlation was observed between the LDL-C measured the end of the stabilization diet period and relative change induced by the soy proteins added in β-sitosterols supplementation (c.c. −0.6021, p=0.038). A similar result was obtained for TC (c.c. −0.6096, p=0.035) and apo B (c.c.=−0.652, p=0.020) plasma level, too. The total and mean (95% IC) LDL-C−DLDL-C fit line is reported in FIG. 3.

The inventor not only made the two compounds available but made the invention regarding the composition, amounts and the weight ratios of the two compounds.

The invention claimed is:

1. A low-dose hypocholesterolemic composition consisting of soya proteins and sitosterol, wherein the soya proteins and the sitosterol are present in a weight ratio of about 6±1.5 of soya proteins to about 1±0.2 of sitosterol; wherein the composition is an optimal daily dose for adults or for children.

2. A composition as claimed in claim 1, wherein the weight ratio is about 6:1.

3. A composition as claimed in claim 1, wherein the weight ratio is about 4:1 in a daily dose for adults of about 8.+−.1 g and/or in a daily dose for children of about 2.+−.0.5 g.

4. A method for treating a patient with moderate, chronic hypercholesterolemia, the method comprising administering to the patient a daily dose of the composition claimed in claim 1, wherein the daily dose is dissolved in water/watery drinks or mixed with pasty/solid food.

5. A method as claimed in claim 4, wherein the method comprises no other modifications of the patient's dietary conduct.

6. A method for treating a patient with high hypercholesterolemia, the method comprising administering to the patient a daily dose of the composition claimed in claim 1, wherein the composition is used as a coadjuvant during drug treatment.

7. A composition for treating hypercholesterolemia, wherein the composition consists of soya proteins and sitosterol, and wherein the soya proteins and the sitosterol are present in the composition in a weight ratio of about 6.+−.1.5 of the soya proteins to about 1.+−.0.2 of the sitosterol.

8. A composition as claimed in claim 1, wherein the weight ratio is about 4:1 to about 6:1.

9. A composition as claimed in claim 8, wherein composition is administered as a daily dose for treating hypercholesterolemia in adults, and wherein the daily dose for adults is about 8.+−.1 g of the composition.

10. A composition as claimed in claim 8, wherein composition is administered as a daily dose for treating hypercholesterolemia in children, and wherein the daily dose for children is about 2.+−.0.5 g.

11. A method for treating a patient with hypercholesterolemia, the method comprising administering to the patient a daily dose of the composition claimed in claim 7.

12. A method as claimed in claim 11, wherein the method comprises no other major or significant modifications of the patient's dietary conduct.

13. A method for treating a patient with hypercholesterolemia, the method comprising administering to the patient a daily dose of the composition claimed in claim 7, wherein the composition is used as a coadjuvant during drug treatment.

14. A low-dose hypercholesterolemic composition consisting of soya proteins, sitosterol and active principles or integrators with coadjuvant, complementary, or useful activity wherein the soya proteins and the sitosterol are present in a weight ratio of about 6.0±1.5 of soya proteins to about 1.0±0.2 of sitosterol; wherein the composition is an optimal daily dose for adults or for children.

15. A low-dose hypercholesterolemic composition consisting of soya proteins, sitosterol, active principles or integrators with coadjuvant, complementary, or useful activity, minerals, salts, vitamins, digestive enzymes, soluble fibers, insoluble fibers, amino acids, or phospholipids wherein the soya proteins and the sitosterol are present in a weight ratio of about 6.0±1.5 of soya proteins to about 1.0±0.2 of sitosterol; wherein the composition is an optimal daily dose for adults or for children.

16. A method of claim 4 further comprising the step of administering a composition comprising excipients that are physiologically suitable.

17. A method of claim 4 further comprising the step of administering a composition comprising diluting agents, e.g. microcrystalline cellulose, lactose, glycine, rice starch, saccharose, fructose, sorbitol; sweeteners; binding agents, e.g. starch water, pvp, methylcellulose; flavoring agents, e.g. citric acid, tartaric acid, sodium chloride, sodium glutamate, menthol; lubricants, e.g. PEG, magnesium stearate, stearic acid, talc; antiaggregating agents; natural and synthetic coloring agents; solubilizers; surfactants; and preservatives.

18. A composition as claimed in claim 1, wherein the composition is a dietary compositions selected from the group consisting of chewable, effervescent, swallowable, and coated tablets, film-coated pills, capsules, soft gelatin capsules, syrup, fruit beverages, granule sachets, fruit gelatins, sweets.

19. A low-dose hypocholesterolemic composition consisting of soya proteins and sitosterol, wherein the soya proteins and the sitosterol are present in a weight ratio of about 6.+−.1.5 of the soya proteins to about 1.+−.0.2 of the sitosterol; and wherein the composition is made up in a daily dose for adults of about 8.+−.1 g and/or in a daily dose for children of about 2.+−.0.5 g.

20. A method for treating a patient with moderate, chronic hypercholesterolemia, the method comprising administering to the patient a daily dose of the composition claimed in claim 19, wherein the daily dose is dissolved in water/watery drinks or mixed with pasty/solid food.

21. A method as claimed in claim 20, wherein the method comprises no other modifications of the patient's dietary conduct.

22. A method for treating a patient with high hypercholesterolemia, the method comprising administering to the patient a daily dose of the composition claimed in claim 19, wherein the composition is used as a coadjuvant during drug treatment.

23. A composition for treating hypercholesterolemia, wherein the composition consists of soya proteins and sitosterol, and wherein the soya proteins and the sitosterol are present in the composition in a weight ratio of about 6.+−.1.5 of the soya proteins to about 1.+−.0.2 of the sitosterol; and wherein the daily dose for adults is about 8.+−.1 g and/or the daily dose for children is about 2.+−.0.5 g.

24. A method for treating a patient with hypercholesterolemia, the method comprising administering to the patient a daily dose of the composition claimed in claim 23.

25. A method as claimed in claim 24, wherein the method comprises no other major or significant modifications of the patient's dietary conduct.

26. A method for treating a patient with hypercholesterolemia, the method comprising administering to the patient a daily dose of the composition claimed in claim 23, wherein the composition is used as a coadjuvant during drug treatment.

* * * * *